US010099157B2

(12) United States Patent
Snyder et al.

(10) Patent No.: US 10,099,157 B2
(45) Date of Patent: Oct. 16, 2018

(54) APATITE IN-SITU RESTORATION

(71) Applicant: Bio-Rad Laboratories, Inc., Hercules, CA (US)

(72) Inventors: Mark A. Snyder, Oakland, CA (US); Kimberly C. Brisack, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 429 days.

(21) Appl. No.: 14/747,221

(22) Filed: Jun. 23, 2015

(65) Prior Publication Data

US 2015/0367252 A1 Dec. 24, 2015

Related U.S. Application Data

(60) Provisional application No. 62/015,894, filed on Jun. 23, 2014, provisional application No. 62/082,017, filed on Nov. 19, 2014.

(51) Int. Cl.
| | |
|---|---|
| *G01N 30/50* | (2006.01) |
| *B01J 20/281* | (2006.01) |
| *B01D 15/20* | (2006.01) |
| *B01D 15/36* | (2006.01) |
| *C01B 25/32* | (2006.01) |
| *C01B 25/455* | (2006.01) |
| *G01N 30/26* | (2006.01) |
| *B01D 15/38* | (2006.01) |
| *B01D 15/42* | (2006.01) |
| *B01J 20/04* | (2006.01) |
| *B01J 20/30* | (2006.01) |
| *B01J 20/34* | (2006.01) |

(52) U.S. Cl.
CPC ......... *B01D 15/203* (2013.01); *B01D 15/361* (2013.01); *B01D 15/3847* (2013.01); *C01B 25/32* (2013.01); *C01B 25/327* (2013.01); *C01B 25/455* (2013.01); *G01N 30/26* (2013.01); *G01N 30/48* (2013.01); *G01N 30/50* (2013.01); *B01J 20/048* (2013.01); *B01J 20/3085* (2013.01); *B01J 20/34* (2013.01)

(58) Field of Classification Search
None
See application file for complete search history.

(56) References Cited

U.S. PATENT DOCUMENTS

| | | | |
|---|---|---|---|
| 3,737,516 A | 6/1973 | Jenner | |
| 4,053,561 A | 10/1977 | Irani | |
| 4,859,342 A | 8/1989 | Shirasawa et al. | |
| 5,332,503 A | 7/1994 | Lee et al. | |
| 5,744,587 A | 4/1998 | Alaska et al. | |
| 5,783,217 A | 7/1998 | Lee et al. | |
| 6,156,178 A | 12/2000 | Mansfield et al. | |
| 6,602,697 B1 | 8/2003 | Cook, III | |
| 7,122,641 B2 | 10/2006 | Vedantham et al. | |
| 7,476,722 B2 | 1/2009 | Vedantham et al. | |
| 7,659,373 B2 | 2/2010 | Burg et al. | |
| 7,767,447 B2 | 8/2010 | Breidenthal et al. | |
| 8,058,407 B2 | 11/2011 | Sun et al. | |
| 8,067,182 B2 | 11/2011 | Kelley et al. | |
| 8,895,707 B2 | 11/2014 | Cummings | |
| 8,951,807 B2 | 2/2015 | Cummings et al. | |
| 2004/0254267 A1 | 12/2004 | Nagae | |
| 2004/0265298 A1 | 12/2004 | Lin | |
| 2005/0107594 A1 | 5/2005 | Sun et al. | |
| 2005/0209100 A1 | 9/2005 | Duval et al. | |
| 2006/0246544 A1 | 11/2006 | Kang et al. | |
| 2007/0060741 A1 | 3/2007 | Kelley et al. | |
| 2009/0047723 A1 | 2/2009 | Jensen et al. | |
| 2009/0186396 A1 | 7/2009 | Gagnon | |
| 2009/0187005 A1 | 7/2009 | Gagnon | |
| 2009/0264651 A1 | 10/2009 | Daly | |
| 2009/0318674 A1 | 12/2009 | Gagnon | |
| 2010/0113751 A1 | 5/2010 | Sun et al. | |
| 2010/0291059 A1 | 11/2010 | Sakuraba et al. | |
| 2012/0149636 A1 | 6/2012 | Kraynov et al. | |
| 2012/0192901 A1 | 8/2012 | Cummings | |
| 2013/0323812 A1 | 12/2013 | Cummings et al. | |

FOREIGN PATENT DOCUMENTS

| | | |
|---|---|---|
| EP | 0256836 A1 | 2/1988 |
| EP | 1081221 A1 | 3/2001 |
| EP | 2138505 B1 | 8/2014 |

(Continued)

OTHER PUBLICATIONS

CFT Ceramic Fluoroapatite. Instruction Manual. Bio-Rad Laboratories, Inc. Jan. 9, 2012 (date obtained from WayBackMachine).
Bankston et al. "pH Transients in hydroxyapatite chromatography columns—Experimental evidence and phenomological modeling", Journal of Chromatography A, 1217 (2010) 2123-2131.
Britsch, "Purification of Flavanone 3 beta-Hydroxylase from *Petunia hybrida*: Antibody preparation and Characterization of a Chemogenetically Defined Mutant", *Archives of Biochemistry and Biophysics*, 276(2):348-354 (1990).
CHT Ceramic Hydroxyapatite: Instruction Manual, 16 pages (2001) http://www.bio-rad.com/cmc_upload/0/000/039/227/Lit-611d.pdf.
Gorbunoff et al.; "The interaction of proteins with hydroxyapatite—I. Role of protein charge and structure"; 1984, *Analytical Biochemistry*, vol. 136, No. 2, pp. 425-432.
Larsen et al., "Solubility Study of the Initial Formation of Calcium Orthophosphates from Aqueous Solutions at pH5-10", *Arch Oral Biol.*, vol. 31, No. 9, pp. 565-572 (1986).

(Continued)

*Primary Examiner* — Kara Graber
(74) *Attorney, Agent, or Firm* — Kilpatrick Townsend & Stockton LLP

(57) ABSTRACT

Disclosed are compositions and methods for regenerating or reducing the deterioration of an apatite solid surface during, or subsequent to, a chromatographic procedure for purifying a target molecule from a sample, by treating the apatite solid surface with a buffered calcium solution, followed by a phosphate buffered solution, followed by an alkaline hydroxide. The buffered calcium solution, phosphate buffered solution, and alkaline hydroxide can be applied subsequent to a bind and elute or flow through purification procedure. The methods provide an increase in resin mass and/or particle strength compared to prior methods.

20 Claims, No Drawings

(56) References Cited

FOREIGN PATENT DOCUMENTS

| WO | 03/059935 A2 | 7/2003 |
|---|---|---|
| WO | 06/099308 A2 | 9/2006 |
| WO | 2008/025748 A1 | 3/2008 |
| WO | 2008/113011 A2 | 9/2008 |
| WO | 2009/017491 A1 | 2/2009 |
| WO | 2010/034442 A1 | 4/2010 |
| WO | 2010/148143 A1 | 12/2010 |

OTHER PUBLICATIONS

Recillas et al., "Studies on the precipitation behavior of calcium phosphate solutions", Journal of Ceramic Processing Research, vol. 13, No. 1, pp. 5-10 (2012).
Schroder et al., "Hydroxyapatite chromatography: altering the phosphate-dependent elution profile of protein as a function of pH", *Analytical Biochemistry*, vol. 313, pp. 176-178 (2003).
International Search Report from PCT/US2011/021158, dated Mar. 17, 2011.
International Search Report from PCT/US2011/048082, dated Mar. 20, 2012.
U.S. Appl. No. 13/006,022, filed Jan. 13, 2011 (25 pages).
U.S. Appl. No. 13/205,354, filed Aug. 8, 2011 (26 pages).
U.S. Appl. No. 13/891,502, filed May 10, 2013 (30 pages).
Extended European Search Report dated Dec. 17, 2014 for EP Application No. 11818724.4, 7 pages.
Extended European Search Report dated Jul. 21, 2014 for EP Application No. 11733384.9, 7 pages.
International Search Report and Written Opinion from PCT/US2012/023512, dated May 10, 2012.
International Search Report and Written Opinion from PCT/US2013/40591, dated Oct. 8, 2013, 12 pages.
International Search Report and Written Opinion from PCT/US2015/037112, dated Sep. 29, 2015.
International Search Report and Written Opinion from PCT/US2015/037116, dated Sep. 16, 2015, 12 pages.
Supplementary European Search Report from EP Appl. No. 15790811.2, dated Feb. 2, 2018.
U.S. Appl. No. 13/006,022, filed Jan. 13, 2011.
U.S. Appl. No. 13/205,354, filed Aug. 8, 2011.
U.S. Appl. No. 13/891,502, filed May 10, 2013.
U.S. Appl. No. 14/598,719, filed Jan. 16, 2015.
U.S. Appl. No. 14/747,162, filed Jun. 23, 2015.
U.S. Appl. No. 14/747,181, filed Jun. 23, 2015.
U.S. Appl. No. 14/932,080, filed Nov. 4, 2015.

APATITE IN-SITU RESTORATION

CROSS-REFERENCES TO RELATED APPLICATIONS

This application claims priority to U.S. Provisional Application No. 62/015,894, filed Jun. 23, 2014; and U.S. Provisional Application No. 62/082,017, filed on Nov. 19, 2014, each of which is incorporated in its entirety herein for all purposes.

BACKGROUND

Apatite solid support surfaces, including hydroxyapatite, ceramic apatite, fluorapatite, and fluoride enhanced apatite, among other apatite solid surfaces, are used for purification of a wide variety of target analytes. Apatite is commonly utilized for purification of biological analytes, including proteins, carbohydrates, polynucleotides, and viral particles. Apatite possesses unique properties as a purification support because it provides metal affinity and cation exchange modalities in a single support. Apatite purification can generally be performed in two ways: (i) flow through purification; and (ii) bind and elute purification.

For flow through purification, traditionally, one (a) equilibrates the column in a suitable buffer; (b) adds a sample to a column under conditions in which impurities bind to the column and the target molecule flows through and is collected, (c) cleans, or strips, the column to remove adsorbed biological compounds with a cleaning/stripping solution (e.g., a high molarity phosphate solution), and (d) regenerates, or sanitizes, the column with a strong alkaline hydroxide solution so that the column can be re-used. In some cases, the strong alkaline hydroxide solution is followed with a lower-molarity rinse for long term storage or re-equilibration.

For bind and elute purification, traditionally, one (a) equilibrates the column in a suitable buffer; (b) adds a sample to a column under conditions in which the target molecule binds to the column, (c) optionally washes the column with one or more solutions; (d) elutes the target molecule (e.g., with a high molarity phosphate and/or alkaline halide solution), e) cleans, or strips, the column to remove adsorbed biological compounds with a cleaning solution (e.g., a high molarity phosphate solution), and (f) regenerates, or sanitizes, the column with a strong alkaline hydroxide solution so that the column can be re-used. In some cases, the strong alkaline hydroxide solution is followed with a lower-molarity rinse for long term storage or re-equilibration.

These traditional apatite purification methods can suffer from poor reproducibility and/or premature apatite deterioration. In some cases, this deterioration is due to the accumulation of hydronium ions (H3O+) on the apatite surface during exposure to equilibration, loading, or chromatography buffers. Hydronium ion accumulation can occur during exposure to alkali metal salts at a pH of 8.0 or below. Hydronium ion accumulation can also occur during exposure to phosphate buffers at a pH of less than about 6.5. Other buffer compositions can also cause hydronium ion accumulation. These hydronium ions are then desorbed upon exposure to a subsequent buffer, such as an elution buffer (e.g., during bind and elute purification) or a cleaning/stripping buffer (e.g., after flow through purification). This desorption causes the resin to deteriorate over time, resulting in a loss of resin mass and/or a decline in the particle strength of the resin.

SUMMARY

Applicants have discovered that the deterioration of an apatite solid surface during, or subsequent to, a chromatographic procedure for purifying a target molecule from a sample can be surprisingly reduced, eliminated, or reversed by treating the apatite solid surface with a buffered calcium solution, followed by a phosphate buffered solution, followed by an alkaline hydroxide. The buffered calcium solution, phosphate buffered solution, and alkaline hydroxide can be applied subsequent to a bind and elute or flow through purification procedure.

In an embodiment, a method of purifying a target analyte with an apatite solid surface comprises (a) contacting the apatite solid surface with the target analyte, thereby separating the target analyte from one or more contaminants; (b) collecting the target analyte; and (c) regenerating the apatite solid surface the regenerating comprising, (i) contacting the apatite solid surface with a buffered calcium solution comprising a calcium ion at a concentration of at least about 1 mM and a non-zwitterionic buffer having a primary, secondary or tertiary amine, wherein the pH of the buffered calcium solution is at least about 7; (ii) contacting the apatite solid surface with a phosphate buffered solution at a pH of at least about 6.5; and (iii) contacting the apatite solid surface with a solution comprising an alkaline hydroxide. In one embodiment, the buffer in (c)(i) is a Tris buffer.

In one embodiment, (a) comprises binding the target analyte to the apatite solid surface, and (b) comprises eluting the target analyte from the apatite solid surface. In some embodiments, (a) comprises binding at least 50% of the target analyte to the apatite solid surface, and (b) comprises eluting the target analyte from the apatite solid surface. In another embodiment, (a) comprises contacting the apatite solid surface to the target analyte, thereby flowing the target analyte through the apatite solid surface, and (b) comprises collecting the target analyte in the flow through. In some embodiments, (a) comprises contacting the apatite solid surface to the target analyte, thereby flowing at least 50% of the target analyte through the apatite solid surface, and (b) comprises collecting the target analyte in the flow through.

In one embodiment, the calcium ion concentration is less than about 50 mM, less than about 25 mM, less than about 15 mM, or less than about 5 mM. In some embodiments, the calcium ion concentration is at least about 1 mM or at least about 25 mM. In some embodiments, the buffered calcium solution comprises at least one component selected from the group consisting of calcium chloride, calcium nitrate, calcium sulfate and calcium lactate. In an embodiment, the buffered calcium solution is at a pH of at least about 7. In some embodiments, the buffered calcium solution is at a pH of between about 7 and about 9. In another embodiment, the phosphate buffered solution comprises a solution containing from about 0.05 M to about 1.0 M phosphate, at a pH of from about 6.5 to about 9. In some cases, the phosphate buffered solution comprises 400 mM phosphate at a pH of 7.0. In some cases, the phosphate buffered solution comprises 500 mM phosphate at a pH of 7.0.

In one embodiment, the hydroxide comprises an alkaline hydroxide. In some cases, the alkaline hydroxide comprises sodium or potassium hydroxide. In one embodiment, the regenerating reverses, decreases or eliminates degradation of the column that occurs during protein purification or column cleaning steps. In another embodiment, the regenerating increases the strength of the apatite solid surface by at least about 1%, 5%, 10%, 15%, 20%, or more.

In one embodiment the regenerating is performed before, or replaces, a phosphate cleaning/stripping step that elutes adsorbed biological compounds. In some cases, the regenerating step is performed after elution of target analyte. In some embodiments, the regenerating step is performed after flowthrough of target analyte.

In one embodiment, the (c)(ii) contacting the apatite solid surface with a solution comprising phosphate at a pH of at least about 6.5 further comprises: contacting the apatite solid surface with a solution comprising phosphate at a concentration of 10 mM, or less than about 10 mM, at a pH of at least about 6.5 or 7; and then contacting the apatite solid surface with a solution comprising phosphate at a concentration of at least about 100 mM, 200 mM, 400 mM, or 500 mM, at a pH of at least about 6.5.

In some embodiments, the method further includes washing the apatite solid surface with a wash solution prior to the regenerating step, the wash solution comprising phosphate at a concentration of 10 mM, or less than about 10 mM, at a pH of at least about 6.5.

In one embodiment, the regenerating consists of (i), a wash, (ii), and (iii).

Definitions

"Apatite" refers to a mineral of phosphate and calcium of the general formula $Ca_5(PO_4)_3(X)$, wherein X is a negatively charged ion. Generally, X is F, Cl, or OH. However, the structure and chemistry of apatite allow for numerous substitutions, including a variety of metal cations (e.g., one or more of K, Na, Mn, Ni, Cu, Co, Zn, Sr, Ba, Pb, Cd, Sb, Y, U, or various rare earth elements) that substitute for Ca in the structure, and anionic complexes (e.g., $AsO_4^{-3}$, $SO_4^{-2}$, $CO_3^{-2}$, $SiO_4^{-4}$, etc.) that substitute for $PO_4^{-3}$.

"Hydroxyapatite" refers to a mixed mode solid support comprising an insoluble hydroxylated mineral of calcium phosphate with the structural formula $Ca_{10}(PO_4)_6(OH)_2$. Its dominant modes of interaction are phosphoryl cation exchange and calcium metal affinity. Hydroxapatite is commercially available in various forms, including but not limited to ceramic, crystalline and composite forms. Composite forms contain hydroxyapatite microcrystals entrapped within the pores of agarose or other beads, or deposited onto membrane surfaces.

"Fluorapatite" refers to a mixed mode support comprising an insoluble fluoridated mineral of calcium phosphate with the structural formula $Ca_{10}(PO_4)_6F_2$. Its dominant modes of interaction are phosphoryl cation exchange and calcium metal affinity. Fluorapatite is commercially available in various forms, including but not limited to ceramic and crystalline composite forms.

An "apatite solid surface" refers to fused nanocrystals (ceramic apatite), microcrystals, or compounded microcrystals of apatite. Apatite solid surfaces include, but are not limited to, hydroxyapatite, or fluorapatite. Ceramic apatites include, but are not limited to, ceramic hydroxyapatite (e.g., CHT™; CaPureHA™ (Tosoh Bioscience LLC)), ceramic fluorapatite or ceramic hydroxyflouroapatite (MPC™). Ceramic apatites are a form of apatite minerals in which nanocrystals are agglomerated into particles and fused at high temperature to create stable ceramic microspheres suitable for chromatography applications. Compounded microcrystals include but are not limited to HA Ultragel® (Pall Corp.). Microcrystals include but are not limited to Bio-Gel HTP, Bio-Gel® HT, DNA-Grade HT (Bio-Rad) and Hypatite C (Clarkson Chromatography).

"Sample" refers to any composition having a target molecule or particle of interest. A sample can be unpurified or partially purified. Samples can include samples of biological origin, including but not limited to blood, or blood parts (including but not limited to serum), urine, saliva, feces, as well as tissues and supernatants of tissue cultures. Samples can also include biomolecules of synthetic origin, including, but not limited to, peptides. Samples can be derived from unpurified, partially purified, or purified cell lysate or spent cell growth media.

"Target molecule" or "target analyte" refers to a molecule or analyte to be detected in a sample. In some embodiments, the target molecule is a peptide, protein (e.g., an antibody, enzyme, growth regulator, clotting factor, or phosphoprotein), polynucleotide (e.g., DNA, such as dsDNA or ssDNA; RNA, such as mRNA or miRNA; or a DNA-RNA hybrid), aptamer, affimer, peptide nucleic acid, carbohydrate, virus, virus-like particle, drug compound, metabolite, or cell.

Deterioration of a resin that occurs upon use can cause the resin particles to lose their strength and thus to break apart into smaller particles causing partial or complete blockage in the column. The deterioration can occur as a chemical breakdown of the apatite, causing a loss of mass which can in turn result in a loss of column volume, a loss in particle strength, an increase in particle breakage, or a combination thereof. In some embodiments of the present invention, such effects can be partially or completely reversed by the present invention. The reversal of deterioration that can be achieved by the practice of the present invention can result in a lower rate of resin mass loss, a lower rate of decline in particle strength, or both. In many cases, the reversal of deterioration can be accompanied by increases in resin mass, particle strength, or both.

Mass of the apatite solid surface can be assayed by, e.g., weighing a dried apatite sample, for example after washing away buffer components and adsorbed biological compounds. Apatite media strength can be assayed by, e.g., measuring resistance to agitational force (e.g., stirring), resistance to sonication, or resistance to compression (e.g., application of a uniaxial compressive force). Resistance to sonication or agitational force can be measured by inspection of the apatite solid surface after the treatment to measure the generation of fines. Resistance to compression can be measured by measuring the force required to compress a given mass of apatite to a constant terminal force setting and determining the compressed distance. Apatite deterioration or degradation can be measured relative to a sample that has not been subjected to an apatite purification (i.e., purification of a target molecule using apatite) or an apatite regeneration procedure.

An "alkaline hydroxide" refers to a metal alkali hydroxide comprising any cation elements in Group I of the periodic table, including, e.g., lithium (Li), sodium (Na), potassium (K), rubidium (Rb), cesium (Cs), and francium (Fr). Thus, exemplary alkaline hydroxides include, for example, NaOH, LiOH, and KOH. "Alkaline hydroxide" may also refer to other cationic hydroxides such as ammonium hydroxide.

Calcium ion for use as a restoration material in the procedures described herein can be supplied by calcium hydroxide or by a soluble calcium salt, typically a salt that is soluble in water. Calcium halides, calcium nitrate, calcium sulfate, and calcium lactate are examples of calcium salts that can be used. An exemplary calcium halide is calcium chloride.

As used herein, the terms "buffer," "buffered," and the like, in the context of a buffered calcium solution refers to a buffer that is compatible with (e.g., does not substantially interact with or precipitate in complex with) calcium under the specified conditions and is employed for the purpose of stabilizing the pH of an aqueous solution at or near a specified value, or within a specified range. As such, generally, the "buffer" in a buffered calcium solution cannot be water. In some embodiments, the "buffer" in a buffered calcium solution is phosphate. In some embodiments, the "buffer" in a buffered calcium solution is Tris. In some embodiments, the "buffer" in a buffered calcium solution used in an in situ regeneration protocol (e.g., after (e.g., immediately after) elution or target analyte flow through, or after (e.g., immediately after) elution or target analyte flow through and a wash) does not contain an alkali metal salt (e.g., sodium chloride), or contains less than about 0.1, 0.05, or 0.01 M alkali metal salt.

Phosphate can be used in a variety of buffers for apatite equilibration, chromatography, elution, cleaning/stripping, or apatite regeneration. Phosphate can be supplied from any soluble phosphate salt, typically a salt that is soluble in water. Alkali metal or alkaline earth metal phosphates are examples, with sodium or potassium phosphate as particularly convenient examples. Alkali or alkaline earth metal phosphate salts can be utilized in mono-, di- or tri-basic forms, or a combination thereof.

As used herein, the term "a", "an" and "the" is intended to mean "one or more." As used herein, the term "about" refers to the recited number and any value within 10% of the recited number. Thus, "about 5" refers to any value between 4.5 and 5.5, including 4.5 and 5.5.

DETAILED DESCRIPTION OF THE INVENTION

I. Introduction

Traditional apatite protein purification procedures generally either do not protect the apatite solid surface from deterioration, or seek to prevent deterioration. Methods that seek to prevent deterioration include the use of one or more common ions (e.g., U.S. application Ser. No. 13/205,354), or the use of a high pH phosphate solution (e.g., U.S. application Ser. No. 10/327,495). The presence of an ionic species in the buffer that is common to a component of the apatite solid surface (a common ion) can suppress leaching of that component from the apatite solid surface. Thus, calcium and/or phosphate buffers are often preferred during apatite equilibration, loading, flow through, elution, or cleaning/stripping. A high pH phosphate solution can function as a common ion, as well as minimizing potentially damaging pH excursions.

Other methods that seek to prevent deterioration include neutralization of accumulated hydronium ions prior to their release from the apatite solid surface during the apatite purification procedure. Neutralization can be performed with a strong base, such as an alkaline hydroxide (e.g., U.S. application Ser. No. 13/363,670). Neutralization can also be performed with a basic amino compound or sulphonated amine compound (e.g., U.S. application Ser. No. 13/006,022). Accumulation of hydronium ions on the apatite surface can occur due to a variety of mechanisms during equilibration, loading, flow through, and washing steps.

In particular, the presence of alkali metal salts can increase, or promote, release of hydronium ions from the surface of apatites. A high pH phosphate solution (e.g., phosphate at a pH of about 6.5 or higher) of sufficient concentration (e.g., 100, 200, 300, 400 mM, or higher), can provide buffering capacity to mitigate the pH shift that commonly occurs during hydronium ion release, and therefore reduce acid solubilization of the apatite. The use of a phosphate buffer at a suitable pH and concentration concurrently with alkali metal salts generally mitigates mass loss to a significant degree. However, media strength can still be significantly decreased. Neutralization of accumulated hydronium ions can reduce the amount of accumulated hydronium ions, and thus reduce degradation during a subsequent step.

The present invention is based on the surprising discovery that an apatite solid surface can be significantly regenerated by treating with a buffered calcium regeneration solution. Generally, the buffered calcium solution is applied after the target molecule has been purified and collected. In some cases, the buffered calcium solution is subsequently washed with a wash solution. In some embodiments, the apatite solid surface is then cleaned/stripped (e.g., with a high molarity phosphate buffer, such as 100, 200, 300, 400, or 500 mM phosphate, or higher). In some cases, the apatite is then treated with a solution of an alkaline hydroxide (e.g., with alkaline hydroxide at a concentration of about 0.1, 0.5, or 1 M). In some cases, the apatite is then treated with a solution having a lower concentration of an alkaline hydroxide than in the previous alkaline hydroxide solution.

The regeneration procedures described herein (e.g., contacting apatite with a buffered calcium solution, then phosphate buffered solution, and then alkaline hydroxide) provide a substantial and surprising degree of regeneration. This substantial and surprising degree of regeneration can be indicated as a reduction, elimination, or reversal of degradation, as measured by change (e.g., loss) in apatite mass or loss in apatite strength. In some cases, regeneration can be indicated as a maintenance, or decrease in loss of chromatographic resolution or selectivity.

In some cases, the regeneration methods described herein can be combined with one or more methods that reduce or prevent degradation, such as those described in the paragraphs above.

II. Methods

Described herein, are apatite regeneration methods for reducing, eliminating, or reversing apatite deterioration by treating the apatite solid surface with a buffered calcium solution, followed by a phosphate buffered solution, followed by an alkaline hydroxide. The buffered calcium solution, phosphate buffered solution, and alkaline hydroxide can be applied subsequent to a bind and elute or flow through purification procedure.

In some embodiments, a sample is contacted with an apatite solid surface (e.g., an equilibrated apatite solid surface), the target molecule is collected (e.g., during flow through purification, or after elution), and the apatite is regenerated by contacting the apatite solid surface with a buffered calcium solution, followed by a phosphate buffered solution, followed by an alkaline hydroxide. In some cases, the apatite solid surface is used multiple times for target analyte purification prior to application of one or more regeneration steps described herein. In some embodiments using a bind and elute purification procedure, at least 50%, 65%, 75%, 85%, or 90% or more of the target molecule binds to the apatite solid surface prior to collecting the target molecule (i.e., prior to elution). In some embodiments using a flow through purification procedure, at least 50%, 65%, 75%, 85%, or 90% or more of the target molecule flows through the apatite solid surface and is collected.

In some embodiments, the apatite solid surface is not washed or rinsed prior to regenerating. In other embodiments, the apatite solid surface is washed or rinsed prior to regenerating. In some cases, the resin is rinsed with a wash solution to remove any excess phosphate ions. One of skill in the art can readily select a suitable wash buffer. Generally, the wash buffer can be at a pH, composition, and concentration that does not substantially leach components of the apatite surface, release accumulated hydronium ions, or generate undesirable precipitate. For example, the wash buffer can be compatible, and thus not precipitate when mixed, with the preceding and subsequent buffer. Suitable washing buffers can include buffer compositions typically used for equilibration, loading, or flow through of apatite. In some cases, the apatite solid surface is washed with a low molarity phosphate buffer (e.g., phosphate at a concentration of less than about 100 mM, 50 mM, 25 mM, 20 mM, 15 mM, 10 mM, or 5 mM). The pH of the wash buffer can be at least about 5, 5.1, 5.2, 5.3, or 5.4, at least about 5.5, at least about 6, or at least about 6.5, 7, or 8. An exemplary wash buffer pH is at least 6.5 or at least 7.0. In some cases, a water wash is applied, and the amounts can vary widely. A typical water wash will be at least about 0.2 resin volumes, and in most cases from about 0.2 to about 1.5 or from about 0.2 to about 2 resin volumes.

The apatite solid surface can then be regenerated. In some cases, the apatite solid surface can be regenerated, e.g., after elution or after flow through. In some cases, the apatite solid surface can be regenerated after a wash, e.g., after application of a wash buffer to remove a flow through or elution buffer.

A. Buffered Calcium Solution

The regeneration begins with contacting the apatite solid surface with a buffered calcium solution. Although, regeneration of the apatite solid surface has been attempted using an unbuffered calcium solution, the present inventors have found that the use of a buffered calcium solution appears to significantly and surprisingly enhance the degree of regeneration obtained. The calcium ion concentration of the buffered calcium solution and the amount of the buffered calcium solution passed through the resin can vary, but will generally be selected as any amount that will reduce, eliminate, or reverse the deterioration of the resin that occurs during apatite use (e.g., during purification, during elution, or during cleaning/stripping).

Without wishing to be bound by theory, it is believed that the buffered calcium solution interacts with the apatite solid surface to generate a loosely bound (e.g., non-covalent) calcium layer on the apatite solid surface. In some cases, this calcium layer replaces some or all (or more than all) of the calcium lost during previous purification steps. Thus, an amount, volume, concentration, etc. of calcium ion, or any other component or aspect of the buffered calcium solution that will reduce, eliminate, or reverse the deterioration of the resin that occurs during apatite use, can be an amount that allows for sufficient formation of a loosely bound calcium layer.

The calcium ion concentration is generally selected to be below the solubility limit of calcium at the pH and temperature of the buffered calcium solution. Moreover, the concentration can vary based on the presence, absence, or concentration of other components in the buffered calcium solution, such as the selected buffering agent, or based on the selected composition of any preceding buffer. In certain embodiments of the concepts herein, best results will be achieved with a calcium ion concentration of from about 5 mM, 5.1 mM, 5.2 mM, 5.3 mM, 5.4 mM, 5.5 mM. 5.6 mM, 5.7 mM, 5.8 mM, 5.9 mM, 6 mM, 6.5 mM, 7 mM, 8 mM, 9 mM, 10 mM, 10.1 mM, 10.2 mM, 10.3 mM, 10.5 mM, or 11 mM to about 15 mM, 20 mM, 25 mM, 30 mM, 40 mM, 50 mM, 75 mM, 100 mM, or 250 mM. In certain embodiments, the calcium ion concentration in the buffered calcium solution is from about 5 mM to about 10 mM, from about 5 mM to about 25 mM, from about 20 mM to about 100 mM, or from about 25 mM to about 50-75 mM, including 5 mM, 5.1 mM, 5.2 mM, 5.3 mM, 5.4 mM, 5.5 mM. 5.6 mM, 5.7 mM, 5.8 mM, 5.9 mM, 6 mM, 6.5 mM, 7, mM, 8 mM, 9 mM, 10 mM, 10.1 mM, 10.2 mM, 10.3 mM, 10.5 mM, 11 mM, 12 mM, 13 mM, 14 mM, 15 mM, 20 mM, 25 mM, 30 mM, 40 mM, 50 mM, 60 mM, 70 mM, 80 mM, 90 mM, 110 mM, 150 mM, 200 mM, 300 mM, or higher.

The volume of the solution needed to achieve the restoration can vary with the calcium ion concentration, but in most cases best results will be achieved with from about 1.0 to about 10.0 resin volumes of solution, and in many cases with about 1, 1.1, 1.2, 1.3, 1.4, 1.5, 1.6, 1.7, 1.8, 1.9, or about 2 resin volumes. In some cases, the volume can be up to about 6 resin volumes, including 2, 3, 4, or 5 or 10 resin volumes. In some cases, the volume is less than 3 column volumes. In some cases, a high calcium ion concentration at a volume that is less than a resin volume (e.g., less than about 0.9, 0.7, 0.5 volumes) can be utilized.

A wide variety of buffers are suitable for the buffered calcium solution for apatite regeneration. In some embodiments, a buffer for the buffered calcium solution that does not appreciably form metal complexes in solution (e.g., does not form a complex with calcium at the pH of the buffer solution) can comprise the buffer component of the buffered calcium solution. In some embodiments, the buffer of the buffered calcium solution contains a primary, secondary, or a tertiary amine and is not zwitterionic. In some embodiments, the buffer of the buffered calcium solution contains a primary, secondary or a tertiary amine and hydroxymethyl groups. In some embodiments, the buffer of the buffered calcium solution is Tris (i.e., tromethamine or tris(hydroxymethyl)aminomethane). In some embodiments, the buffer of the buffered calcium solution is bis(2-hydroxyethyl)-amino-tris(hydroxymethyl)-methane), or 1,3-bis(tris(hydroxymethyl) methylamino) propane, triethylamine, triethanolamine or trimethylamine.

The buffer concentration in the buffered calcium solution can vary, but will generally be selected as a concentration that is at least as high as the calcium ion concentration of the solution. Moreover, the concentration can vary based on the selected buffering agent, or the selected composition of any preceding buffer. Thus, the ratio of the buffer concentration to the calcium ion concentration is generally at least about 0.2, e.g., 0.2, 0.5, 1, 1.1, 1.2, 1.3, 1.4, 1.5, 1.6, 1.7, 1.8, 1.9, 2, 2.1, 2.2, 2.5, 3, 4, 5, 6, 7, 8, 9, 10, or higher. Generally, the buffer concentration is also selected such that it is below the solubility limit of the buffering agent. In some cases, preferred buffering agents include those that have a high solubility limit.

The pH of the buffered calcium solution can vary, but will generally be selected as any amount that will reduce, eliminate, or reverse deterioration of the resin that occurs during apatite use (e.g., during purification, during elution, or during cleaning/stripping). Moreover, the pH can vary based on the selected apatite solid surface, the selected buffering agent, the selected concentration of one or more components, or the selected composition of any preceding buffer. Typically, the pH is, or is at least about, 5, 5.1, 5.2, 5.3, 5.4, 5.5, 5.6, 6, 6.2, 6.5, 7, 7.5, 8, 8.5 or 9. In some embodiments, the pH is, or is at least about, 5.5, 6, 6.5, 7, 7.5, 8, 8.5 or 9.

In some embodiments, the pH is 5.5, 6, 6.5, 7, 7.5, 8, 8.5 or 9. In some embodiments, the pH is 5.1, 5.2, 5.3, or 5.4. In some cases, the pH is 5.3. In some cases, the pH is 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, or 9. In some cases, the pH is 7.0. In some cases, the pH is 8.0. In some cases, the pH is 9.0. In some cases, the pH is 5.6. In some cases, the pH is 6.2. In some cases, the pH is 5.4.

In some embodiments, the buffer of the buffered calcium solution is a phosphate buffer. In such cases, the calcium and phosphate concentrations and the pH of the solution can be selected to provide regeneration while avoiding precipitant formation, or avoiding a supersaturated solution. For example, the pH of the phosphate buffered calcium solution can be selected to be sufficiently low (e.g., a pH of about, or less than about, 6.5, 6.4, 6.3, 6.2, 6.1, 6, 5.9, 5.8, 5.7, 5.6, 5.5, 5.4, 5.3, 5.2, 5.1, or 5). In some cases, the pH is 5.1, 5.2, 5.3, 5.4, or 5.5. In some cases, the pH is 5.3. As another example, the calcium concentration of the phosphate buffered calcium solution can be about, or less than about, 50 mM, 40 mM, 35 mM, 30 mM, 25 mM, 20 mM, 15 mM, 10 mM, 7 mM, 6 mM, 5.9 mM, 5.8 mM, 5.7 mM, 5.6 mM, 5.5 mM, 5.4 mM, 5.3 mM, 5.2 mM, 5.1 mM, or 5 mM. In some cases, the calcium concentration of the phosphate buffered solution is, or is about, 15 mM, 14 mM, 13 mM, 12 mM, 11 mM, 10.5 mM, 10.4 mM, 10.3 mM, 10.2 mM, 10.1 mM, 10 mM, or 9.5 mM. In some cases, the calcium concentration is 10 or 10.2 mM. In some cases, the calcium concentration is 10 mM. As another example, the phosphate concentration of the phosphate buffered calcium solution can be about, or less than about, 50 mM, 40 mM, 35 mM, 30 mM, 29 mM, 28 mM, 27 mM, 26 mM, 25 mM, 24 mM, 23 mM, 21 mM, 20 mM, 18 mM, 17 mM, 16 mM, or 15 mM. In some cases, the use of a phosphate buffered calcium solution provides regeneration with or without a preceeding or subsequent high molarity (e.g., 0.1, 0.2, 0.3, 0.4, 0.5, 0.6, 0.7, 0.8, 0.9, or 1 M) phosphate buffer step.

In some embodiments, the apatite solid surface is in a column, e.g., a chromatography column or membrane holder, and the buffered calcium solution can be applied to the apatite solid surface at a flow rate. The flow rate can vary, but will generally be selected as any rate that will reduce, eliminate, or reverse deterioration of the resin that occurs during apatite use (e.g., during purification, during elution, or during cleaning/stripping). Suitable flow rates, include rates that are typically used during equilibration, loading, elution, cleaning/stripping, sanitization, or rinsing of apatite. An exemplary flow rate is 400 cm/hr. In some cases, the flow rate is substantially lower than 400 cm/hr (e.g., 300, 200, 100, or 50 cm/hr, or less). The use of a low flow rate can allow a greater contact time between the apatite solid surface and the buffered calcium solution. A low flow rate can be particularly preferred when the concentration of calcium or buffering agent, or the volume of the buffered calcium solution, is low. A low flow rate can also be preferred when the buffered calcium solution, or the preceding solution, is viscous or the column is fouled with adsorbed biological compounds. Alternatively, the flow rate can be higher than 400 cm/hr (e.g., 500, 600, 700, or 8000 cm/hr, or more). In some cases, the formation of a loosely bound layer of calcium is rapid and a high flow rate can advantageously reduce the time required for apatite regeneration.

In some embodiments, the apatite solid surface is contacted with the buffered calcium solution in a batch format. In a batch format, the buffered calcium solution can be applied by pouring the buffered calcium solution into a slurry or suspension of the apatite solid surface, or pouring a slurry of the apatite solid surface into the buffered calcium solution. The contact time can vary, but will generally be selected as any time that will reduce, eliminate, or reverse deterioration of the resin that occurs during apatite use (e.g., during purification, during elution, or during cleaning/stripping).

In some embodiments, the apatite solid surface is then washed or rinsed. One of skill in the art can readily select a suitable wash buffer. In some cases, the resin is treated with a wash solution between the individual regeneration treatments to remove any excess calcium, phosphate, or hydroxide ions. Generally, the wash buffer can be at a pH, composition, and concentration that does not substantially leach components of the apatite surface, release accumulated hydronium ions, or generate undesirable precipitate. For example, the wash buffer can be compatible, and thus not precipitate when mixed, with the preceding and subsequent buffer. As another example, the wash buffer can be selected that does not leach any loosely bound calcium layer formed during the contacting of the apatite solid surface with the buffered calcium solution. Suitable washing buffers can include buffer compositions typically used for equilibration, loading, or flow through of apatite. In some cases, the apatite solid surface is washed with a low molarity phosphate buffer (e.g., phosphate at a concentration of less than about 100 mM, 50 mM, 25 mM, 20 mM, 15 mM, 10 mM, or 5 mM). The pH of the wash buffer can be at least about 5, at least about 5.5, at least about 6, or at least about 6.5, 7, or 8. In some cases, a water wash is applied, and the amounts can vary widely. A typical water wash will be at least about 0.2 resin volumes, and in most cases from about 0.2 to about 1.5 or from about 0.2 to about 2 resin volumes.

B. Phosphate Buffered Solution

The apatite solid surface can then be contacted with a phosphate containing buffer after the apatite has been contacted with a buffered calcium solution. In some cases, an intervening wash step is applied between the buffered calcium solution and the phosphate containing buffer. In some embodiments, the apatite surface is cleaned with a phosphate solution to remove residual proteins and contaminants. The phosphate concentration of the phosphate containing buffer and the amount of the phosphate containing buffer passed through the resin can vary, but will generally be selected as any amount that will reduce, eliminate, or reverse the deterioration of the resin that occurs during apatite use (e.g., during purification, during elution, or during cleaning/stripping). Without wishing to be bound by theory, it is believed that the phosphate containing buffer interacts with the apatite solid surface, or a loosely bound calcium layer formed during contact with the buffered calcium solution, to generate a loosely bound (e.g., non-covalent) phosphate layer on the apatite solid surface. In some cases, this phosphate layer replaces some or all (or more than all) of the phosphate lost during previous purification steps. Thus, an amount, volume, concentration, etc. of phosphate, or any other component or aspect of the phosphate containing buffer that will reduce, eliminate, or reverse the deterioration of the resin that occurs during apatite use, can be an amount that allows for sufficient formation of a loosely bound phosphate layer.

The phosphate concentration of the phosphate containing buffer is generally selected to be below the solubility limit of the phosphate at the pH and temperature of the buffer. Moreover, the concentration can vary based on presence or absence of other components of the buffer, or the selected composition of any preceding buffer. In certain embodiments of the concepts herein, best results will be achieved with a phosphate concentration of from about 5 mM to about 1, 1.5, or 2 M; from about 20 mM to about 1.5 M; or from about 25 mM to about 1 M; from about 50 mM to about 1 M; including at least about, or about, 5 mM, 10 mM, 15 mM, 20 mM, 25 mM, 30 mM, 40 mM, 50 mM, 60 ppm, 70 mM, 80 mM, 90 mM, 100 mM, 110 mM, 150 mM, 200 mM, 300 mM, 500 mM, 750 mM, 1 M, or higher. In some cases, the phosphate concentration is 5 mM, 10 mM, 15 mM, 20 mM, 25 mM, 30 mM, 40 mM, 50 mM, 60 ppm, 70 mM, 80 mM, 90 mM, 100 mM, 110 mM, 150 mM, 200 mM, 300 mM, 500 mM, 750 mM, 1 M, or higher. In some cases, the phosphate concentration is from, or from about, 0.1 M or 0.2 M to, or to about, 0.4 M, 0.5 M, or 1 M. In some cases, the column is contacted with a low concentration phosphate buffer (e.g., 2, 5, 10, 15, 20, or 25 mM) and then a high concentration phosphate buffer (e.g., 30; 50; 75; 100; 250; 500; 750; 1,000; 1,500; or 2,000 mM). In some cases, the use of a low concentration phosphate buffer followed by a high concentration phosphate buffer can avoid potential incompatibility (e.g., precipitation) between the buffered calcium solution and the high concentration phosphate buffer.

In some embodiments, the phosphate containing buffer includes an alkali metal salt. In an embodiment, the phosphate containing buffer includes a low concentration of sodium chloride, e.g., from about 100 mM to about 200 mM sodium chloride. In some cases, the phosphate containing buffer includes 100 mM, 150 mM, or 200 mM sodium chloride.

The pH of the phosphate containing buffer and the amount of the phosphate containing buffer passed through the resin can vary, but will generally be selected as any pH that will reduce, eliminate, or reverse the deterioration of the resin that occurs during apatite use (e.g., during purification, during elution, or during cleaning/stripping). Exemplary pH values suitable for apatite regeneration with a phosphate containing buffer include any pH that is at least about 5, at least about 5.5, at least about 6, at least about 6.5, at least about 7, at least about 7.5, at least about 8, or at least about 8.5, or higher. In some cases, the pH of the phosphate containing buffer is 5, 5.5, 6, 6.5, 7, 7.5, 8, 8.5, 9, 9.5, 10, or higher.

The volume of the solution needed to achieve the restoration can vary with the phosphate ion concentration, but in most cases best results will be achieved with from about 1.0 to about 10.0 resin volumes of solution, and in many cases with about 1, 1.1, 1.2, 1.3, 1.4, 1.5, 1.6, 1.7, 1.8, 1.9, or about 2 resin volumes. The volume can be up to about 6 resin volumes, including 2, 3, 4, or 5 resin volumes. In some cases, a high phosphate concentration at a volume that is less than a resin volume (e.g., less than about 0.9, 0.7, 0.5 volumes) can be utilized.

In some embodiments, the apatite solid surface is in a column, e.g., a chromatography column or membrane holder, and the phosphate containing buffer can be applied to the apatite solid surface at a flow rate. The flow rate can vary, but will generally be selected as any rate that will reduce, eliminate, or reverse deterioration of the resin that occurs during apatite use (e.g., during purification, during elution, or during cleaning/stripping). Suitable flow rates, include rates that are typically used during equilibration, loading, elution, cleaning/stripping, sanitization, or rinsing of apatite. An exemplary flow rate is 400 cm/hr. In some cases, the flow rate is substantially lower than 400 cm/hr (e.g., 300, 200, 100, or 50 cm/hr, or less). The use of a low flow rate can allow a greater contact time between the apatite solid surface and the phosphate containing buffer. A low flow rate can be particularly preferred when the concentration of phosphate, or the volume of the phosphate containing buffer, is low. A low flow rate can also be preferred when the phosphate containing buffer, or the preceding solution, is viscous or the column is fouled with adsorbed biological compounds. Alternatively, the flow rate can be higher than 400 cm/hr. In some cases, the formation of a loosely bound layer of phosphate is rapid and a high flow rate can advantageously reduce the time required for apatite regeneration.

In some embodiments, the apatite solid surface is contacted with the phosphate containing buffer in a batch format. In a batch format, the phosphate containing buffer can be applied by pouring the phosphate containing buffer into a slurry or suspension of the apatite solid surface, or pouring a slurry of the apatite solid surface into the phosphate containing buffer. The contact time can vary, but will generally be selected as any time that will reduce, eliminate, or reverse deterioration of the resin that occurs during apatite use (e.g., during purification, during elution, or during cleaning/stripping).

In some embodiments, the apatite solid surface is then washed or rinsed. In other embodiments, the apatite solid surface is not washed or rinsed after regeneration treatment with a phosphate containing buffer. One of skill in the art can readily select a suitable wash buffer. In some cases, the resin is treated with a wash solution to remove any excess phosphate ions. Generally, the wash buffer is at a pH, composition, and concentration that does not substantially leach components of the apatite surface, release accumulated hydronium ions, or generate undesirable precipitate. For example, the wash buffer can be compatible, and thus not precipitate when mixed, with the preceding and subsequent buffer. As another example, the wash buffer can be selected that does not leach any loosely bound calcium layer formed during the contacting of the apatite solid surface with the buffered calcium solution. Suitable washing buffers can include buffer compositions typically used for equilibration, loading, or flow through of apatite. In some cases, the apatite solid surface is washed with a low molarity phosphate buffer (e.g., phosphate at a concentration of less than about 100 mM, 50 mM, 25 mM, 20 mM, 15 mM, 10 mM, or 5 mM). The pH of the wash buffer can be at least about 5, at least about 5.5, at least about 6, or at least about 6.5, 7, or 8. In some cases, a water wash is applied, and the amounts can vary widely. A typical water wash will be at least about 0.2 resin volumes, and in most cases from about 0.2 to about 1.5 or from about 0.2 to about 2 resin volumes.

In some embodiments, a preferred degree of regeneration can be achieved by performing one or more steps of buffered calcium solution treatment subsequent to, or followed by, one or more steps of phosphate containing buffer treatment. In some cases, one or more of multiple steps of buffered calcium solution treatment or phosphate containing buffer treatment are preceded by or followed by a wash.

In some embodiments, the buffered calcium solution treatment and/or the phosphate containing buffer treatment is applied after elution or flow through of a target analyte. For example an apatite surface can be equilibrated, contacted with a target analyte, the target analyte can be eluted or collected in the flow through, and then the regeneration protocol can be applied. As described herein, exemplary regeneration protocols can include, but are not limited to, those in which a buffered calcium solution is contacted with the apatite solid surface and then a phosphate buffer is contacted with the apatite solid surface. An alkaline hydroxide treatment can be applied after the apatite is contacted with the buffered calcium and phosphate regeneration solutions.

C. Hydroxide

The hydroxide ion treatment is applied as the last treatment step of the apatite solid surface regeneration. Any soluble form of hydroxide ion can be used, preferably a water-soluble form is used. In some cases, alkali metal hydroxides, such as sodium, potassium, or lithium hydroxide, are particularly convenient. In some cases, an alkaline hydroxide solution, such as ammonium hydroxide, can be used. In some embodiments, at least one alkali metal hydroxide and/or an alkaline hydroxide can be used. As in the cases of the calcium ion and the phosphate ion, the concentration and quantity of hydroxide ion solution can vary. Without wishing to be bound by theory, it is believed that the hydroxide interacts with the apatite solid surface, or loosely bound (e.g., non-covalently bound) calcium, phosphate, or calcium and phosphate layer(s) formed during contact with the buffered calcium solution and/or phosphate containing buffer, to convert the loosely bound (e.g., non-covalently bound) minerals into apatite, thus providing a regenerated surface. In some cases, this regenerated surface replaces some or all (or more than all) of the calcium, phosphate, or calcium phosphate lost during previous purification steps. Thus, an amount, volume, concentration, etc. of hydroxide that will reduce, eliminate, or reverse the deterioration of the resin that occurs during apatite use, can be an amount that allows for sufficient conversion of loosely bound calcium, phosphate, or calcium phosphate to apatite. The hydroxide ion can also clean the resin of residual proteins and contaminants and can also serve as a sanitization or storage solution.

The hydroxide ion concentration can be from about 0.005 or 0.01 M to about 5 M; about 0.1 M to about 4.0 M, and in many cases from about 0.3 M to about 3.0 M, including 0.2 M, 0.5 M, 0.75 M, 1.0 M, 1.25 M, 1.5 M, 2.0 M, or 2.5 M. Suitable volumes of hydroxide ion containing treatment solution range from about 1.0 to about 20.0 resin volumes, and in many cases from about 1.5 to about 10.0 resin volumes, including 2, 3, 4, 5, 6, 7, 8, or 9 volumes. In some cases, a high hydroxide concentration at a volume that is less than a resin volume (e.g., less than about 0.9, 0.7, 0.5 volumes) can be utilized.

Following hydroxide treatment, the resin can be washed or equilibrated with a suitable buffer. In some cases, the resin is equilibrated, or washed and then equilibrated, with a loading buffer. For example, the resin can be equilibrated with 10 mM phosphate buffer, pH 6.5 to equilibrate the column for subsequent protein purification. In some cases, the resin is equilibrated, or washed and then equilibrated, with a storage buffer. For example, the resin can be equilibrated with 0.1 M NaOH and then stored.

EXAMPLES

The following examples are provided by way of illustration only and not by way of limitation. Those of skill in the art will readily recognize a variety of non-critical parameters that could be changed or modified to yield essentially the same or similar results.

All the columns used in the following examples measured 5 cm in length and 2.2 cm in internal diameter, with an internal column volume of 19 mL. To pack each column, 11.97 grams of ceramic hydroxyapatite Type I in 40-micron particles was suspended in 0.2 M NaPO4, pH 7. The slurry was transferred to an empty column which was packed by tapping and vacuum suction from the bottom. The mobile phase flow rate through each column was 28.5 mL/minute (450 cm/hour). Mobile phase entry was from the top of each column.

Example 1

This example illustrates the result of incorporating a Tris-buffered calcium regeneration solution in an in situ regeneration protocol. The apatite resin was exposed to a series of cycles that simulate conditions encountered in a bind and elute protein separation, but without loading and eluting protein. In this example, the elution step of the bind and elute purification protocol utilized a high concentration of phosphate in a phosphate buffered saline solution.

The description and conditions for the experiments are listed in Tables I through IV below. A series of 16 consecutive cycles were performed, each cycle consisting of the steps listed in each table. Table I simulates a control purification protocol without column restoration. Tables II-IV are restoration protocols that use an increasing concentration of Tris (i.e., 20 mM Tris, 50 mM Tris, and 100 mM Tris in Table II, Table III, and Table IV, respectively) in the Tris-buffered calcium regeneration solution in step 7. Also, the restoration protocols in Tables II and III use 10 mM CaCl2 and the restoration protocol in Table IV uses 50 mM CaCl2 in the Tris-buffered calcium regeneration solution.

TABLE I

Control Treatment Protocol

| Step | Description | Mobile Phase | Column Volumes | Volume in mL |
|---|---|---|---|---|
| 1 | Pre-Equilibration/Regeneration | 500 mM NaPO4, 150 mM NaCl, pH 7.0 | 3 | 57 |
| 2 | Equilibration | 10 mM NaPO4, 150 mM NaCl, pH 7.0 | 3 | 57 |
| 3 | Product load | 10 mM NaPO4, 150 mM NaCl, pH 7.0 | 3 | 57 |
| 4 | Wash | 80 mM NaPO4, 150 mM NaCl, pH 7.0 | 3 | 57 |
| 5 | Elution | 150 mM NaPO4, 150 mM NaCl, pH 7.0 | 5 | 95 |
| 6 | Regeneration | 500 mM NaPO4, 150 mM NaCl, pH 7.0 | 3 | 57 |
| 7 | Sanitization | 1M NaOH | 2 | 38 |

TABLE II

| | | Column Restoration Protocol | Amount | |
|---|---|---|---|---|
| Step | Description | Mobile Phase | Column Volumes | Volume in mL |
| 1 | Pre-Equilibration/Regeneration | 500 mM NaPO4, 150 mM NaCl, pH 7.0 | 3 | 57 |
| 2 | Equilibration | 10 mM NaPO4, 150 mM NaCl, pH 7.0 | 3 | 57 |
| 3 | Product load | 10 mM NaPO4, 150 mM NaCl, pH 7.0 | 3 | 57 |
| 4 | Wash | 80 mM NaPO4, 150 mM NaCl, pH 7.0 | 3 | 57 |
| 5 | Elution | 150 mM NaPO4, 150 mM NaCl, pH 7.0 | 5 | 95 |
| 6 | Post-elution wash | 10 mM NaPO4, 150 mM NaCl, pH 7.0 | 1.5 | 28.5 |
| 7 | In-Situ Restoration (ISR) | 20 mM Tris, 50 mM CaCl2, pH 8 | 2 | 38 |
| 8 | Post-ISR Wash | 10 mM NaPO4, 150 mM NaCl, pH 7.0 | 1.5 | 28.5 |
| 9 | Regeneration | 500 mM NaPO4, 150 mM NaCl, pH 7.0 | 3 | 57 |
| 10 | Sanitization | 1M NaOH | 2 | 38 |

TABLE III

| | | Column Restoration Protocol | Amount | |
|---|---|---|---|---|
| Step | Description | Mobile Phase | Column Volumes | Volume in mL |
| 1 | Pre-Equilibration/Regeneration | 500 mM NaPO4, 150 mM NaCl, pH 7.0 | 3 | 57 |
| 2 | Equilibration | 10 mM NaPO4, 150 mM NaCl, pH 7.0 | 3 | 57 |
| 3 | Product load | 10 mM NaPO4, 150 mM NaCl, pH 7.0 | 3 | 57 |
| 4 | Wash | 80 mM NaPO4, 150 mM NaCl, pH 7.0 | 3 | 57 |
| 5 | Elution | 150 mM NaPO4, 150 mM NaCl, pH 7.0 | 5 | 95 |
| 6 | Post-elution wash | 10 mM NaPO4, 150 mM NaCl, pH 7.0 | 1.5 | 28.5 |
| 7 | In-Situ Restoration (ISR) | 50 mM Tris, 50 mM CaCl2, pH 8 | 2 | 38 |
| 8 | Post-ISR Wash | 10 mM NaPO4, 150 mM NaCl, pH 7.0 | 1.5 | 28.5 |
| 9 | Regeneration | 500 mM NaPO4, 150 mM NaCl, pH 7.0 | 3 | 57 |
| 10 | Sanitization | 1M NaOH | 2 | 38 |

TABLE IV

| | | Column Restoration Protocol | Amount | |
|---|---|---|---|---|
| Step | Description | Mobile Phase | Column Volumes | Volume in mL |
| 1 | Pre-Equilibration/Regeneration | 500 mM NaPO4, 150 mM NaCl, pH 7.0 | 3 | 57 |
| 2 | Equilibration | 10 mM NaPO4, 150 mM NaCl, pH 7.0 | 3 | 57 |
| 3 | Product load | 10 mM NaPO4, 150 mM NaCl, pH 7.0 | 3 | 57 |
| 4 | Wash | 80 mM NaPO4, 150 mM NaCl, pH 7.0 | 3 | 57 |
| 5 | Elution | 150 mM NaPO4, 150 mM NaCl, pH 7.0 | 5 | 95 |
| 6 | Post-elution wash | 10 mM NaPO4, 150 mM NaCl, pH 7.0 | 1.5 | 28.5 |
| 7 | In-Situ Restoration (ISR) | 100 mM Tris, 50 mM CaCl2, pH 8 | 2 | 38 |
| 8 | Post-ISR Wash | 10 mM NaPO4, 150 mM NaCl, pH 7.0 | 1.5 | 28.5 |
| 9 | Regeneration | 500 mM NaPO4, 150 mM NaCl, pH 7.0 | 3 | 57 |
| 10 | Sanitization | 1M NaOH | 2 | 38 |

The particle mass and particle strength of the resin was measured before the first cycle and after the last cycle for each protocol described in Tables I-IV. Uniaxial confined bulk compression (UCBC) was used to determine the particle strength. Note that the resin sample used in the Table IV protocol was tested by a different UCBC method than the resin samples in Tables I-III. Table V lists the results for the protocols described in Tables I-IV.

TABLE V

Results

| Resin Sample | Table Reference | Mass Change, % | Strength Change, % |
| --- | --- | --- | --- |
| Control Protocol | I | −1.5 | −16 |
| ISR with 20 mM Tris, 10 mM CaCl2, pH 8 | II | 2.3 | 8 |
| ISR with 50 mM Tris, 10 mM CaCl2, pH 8 | III | 3.9 | 15 |
| ISR with 100 mM Tris, 50 mM CaCl2, pH 8 | IV | 15 | Increase |

The results in Table V indicate that the resin treated with a control protocol experienced degradation as evidenced by a loss of mass and particle strength. Hydroxyapatite obtained from a column using the column restoration protocols in Tables II-IV gained in mass and particle strength compared to the control protocol. Note that, because a different UCBC method was used to determine the particle strength for the resin from the Table IV protocol, a direct comparison with the resin from the other protocols could not be made. These results demonstrate that the use of a Tris buffered calcium solution, followed by application of a phosphate buffer and then a hydroxide provides a surprising degree of regeneration, as evidenced by both an increase in mass and particle strength. The results also indicate a surprising degree of regeneration when a regeneration protocol follows an elution step utilizing a high concentration of phosphate.

Example 2

This example illustrates the result of incorporating a Tris-buffered calcium regeneration solution in an in situ regeneration protocol. The apatite resin was exposed to a series of cycles that simulate conditions encountered in a bind and elute protein separation, but without loading and eluting protein. In this example, the bind and elute purification protocol utilized an alkali metal salt in the elution step.

The description and conditions for the experiments are listed in Tables VI through IX below. A series of 16 consecutive cycles were performed, each cycle consisting of the steps listed in each table. Table VI simulates a control purification protocol without column restoration. Tables VII-IX are restoration protocols that use an increasing concentration of Tris (i.e., 20 mM Tris, 50 mM Tris, and 100 mM Tris in Table VII, Table VIII, and Table IX, respectively) in the Tris-buffered calcium regeneration solution in step 7. Also, all the restoration protocols in Tables VII-IX use 10 mM CaCl2 in the Tris-buffered calcium regeneration solution.

TABLE VI

Control Treatment Protocol

| | | | Amount | |
| --- | --- | --- | --- | --- |
| Step | Description | Mobile Phase | Column Volumes | Volume in mL |
| 1 | Pre-Equilibration/Regeneration | 400 mM NaPO4, pH 7.0 | 4 | 76 |
| 2 | Equilibration/Product Load | 5 mM NaPO4, 100 mM NaCl, pH 6.5 | 15 | 285 |
| 3 | Elution | 5 mM NaPO4, 550 mM NaCl, pH 6.5 | 4 | 76 |
| 4 | Wash | 5 mM NaPO4, 100 mM NaCl, pH 6.5 | 1 | 19 |
| 5 | Regeneration | 400 mM NaPO4, pH 7.0 | 3 | 57 |
| 6 | Sanitization | 1M NaOH | 3 | 57 |

TABLE VII

Column Restoration Protocol

| | | | Amount | |
| --- | --- | --- | --- | --- |
| Step | Description | Mobile Phase | Column Volumes | Volume in mL |
| 1 | Pre-Equilibration/Regeneration | 400 mM NaPO4, pH 7.0 | 4 | 76 |
| 2 | Equilibration/Product Load | 5 mM NaPO4, 100 mM NaCl, pH 6.5 | 15 | 285 |
| 3 | Elution | 5 mM NaPO4, 550 mM NaCl, pH 6.5 | 4 | 76 |
| 4 | In-Situ Restoration (ISR) | 20 mM Tris, 10 mM CaCl2, pH 8 | 2 | 38 |
| 5 | Post-ISR Wash | 5 mM NaPO4, 100 mM NaCl, pH 6.5 | 1.5 | 28.5 |

TABLE VII-continued

Column Restoration Protocol

| | | | Amount | |
|---|---|---|---|---|
| Step | Description | Mobile Phase | Column Volumes | Volume in mL |
| 6 | Regeneration | 400 mM NaPO4, pH 7.0 | 3 | 57 |
| 7 | Sanitization | 1M NaOH | 3 | 57 |

TABLE VIII

Column Restoration Protocol

| | | | Amount | |
|---|---|---|---|---|
| Step | Description | Mobile Phase | Column Volumes | Volume in mL |
| 1 | Pre-Equilibration/Regeneration | 400 mM NaPO4, pH 7.0 | 4 | 76 |
| 2 | Equilibration/Product Load | 5 mM NaPO4, 100 mM NaCl, pH 6.5 | 15 | 285 |
| 3 | Elution | 5 mM NaPO4, 550 mM NaCl, pH 6.5 | 4 | 76 |
| 4 | In-Situ Restoration (ISR) | 50 mM Tris, 10 mM CaCl2, pH 8 | 2 | 38 |
| 5 | Post-ISR Wash | 5 mM NaPO4, 100 mM NaCl, pH 6.5 | 1.5 | 28.5 |
| 6 | Regeneration | 400 mM NaPO4, pH 7.0 | 3 | 57 |
| 7 | Sanitization | 1M NaOH | 3 | 57 |

TABLE IX

Column Restoration Protocol

| | | | Amount | |
|---|---|---|---|---|
| Step | Description | Mobile Phase | Column Volumes | Volume in mL |
| 1 | Pre-Equilibration/Regeneration | 400 mM NaPO4, pH 7.0 | 4 | 76 |
| 2 | Equilibration/Product Load | 5 mM NaPO4, 100 mM NaCl, pH 6.5 | 15 | 285 |
| 3 | Elution | 5 mM NaPO4, 550 mM NaCl, pH 6.5 | 4 | 76 |
| 4 | In-Situ Restoration (ISR) | 100 mM Tris, 10 mM CaCl2, pH 8 | 2 | 38 |
| 5 | Post-ISR Wash | 5 mM NaPO4, 100 mM NaCl, pH 6.5 | 1.5 | 28.5 |
| 6 | Regeneration | 400 mM NaPO4, pH 7.0 | 3 | 57 |
| 7 | Sanitization | 1M NaOH | 3 | 57 |

The particle mass and particle strength was measured before the first cycle and after the last cycle for each protocol described in Tables VI-IX. Uniaxial confined bulk compression was used to determine the particle strength. Table X lists the results for the protocols described in Tables VI-IX.

TABLE X

Results

| Resin Sample | Table Reference | Mass Change, % | Strength Change, % |
|---|---|---|---|
| Control Protocol | VI | −2.6 | −28 |
| ISR with 20 mM Tris, 10 mM CaCl2, pH 8 | VII | 1.0 | −6 |
| ISR with 50 mM Tris, 10 mM CaCl2, pH 8 | VIII | 2.4 | −2 |
| ISR with 100 mM Tris, 10 mM CaCl2, pH 8 | IX | 2.8 | 11 |

The results in Table X indicate that the resin treated with a control protocol experienced degradation as evidenced by a loss of mass and particle strength. Hydroxyapatite obtained from a column using the restoration protocols in Tables VII-IX exhibited a gain in mass when compared to the control protocol in Table VI. Only hydroxyapatite obtained from a column using a restoration protocol having 100 mM Tris (Table IX) exhibited a gain in particle strength when compared to the control protocol. The results in Table X demonstrate a surprising degree of regeneration when a regeneration protocol having a high concentration of Tris in the Tris buffered calcium solution follows an elution step utilizing a high concentration of alkali metal salt.

Example 3

This example illustrates the result of incorporating a Tris-buffered calcium regeneration solution in an in situ regeneration protocol. The apatite resin was exposed to a series of cycles that simulate conditions encountered in a flow through purification protocol, without loading protein. In this example, a phosphate buffered sodium chloride solution was used in the flow through step.

The description and conditions for the experiments are listed in Tables XI through XIV below. A series of 16 consecutive cycles were performed, each cycle consisting of the steps listed in each table. Table XI simulates a control purification protocol without column restoration. Tables XII-XIV are restoration protocols that use an increasing concentration of Tris (i.e., 20 mM Tris, 50 mM Tris, and 100 mM Tris in Table XII, Table XIII, and Table IV, respectively) in the Tris-buffered calcium regeneration solution in step 7. All the restoration protocols in Tables XII-XIV use 10 mM CaCl2 in the Tris-buffered calcium regeneration solution.

TABLE XI

Control Treatment Protocol

| Step | Description | Mobile Phase | Column Volumes | Volume in mL |
|---|---|---|---|---|
| 1 | Pre-Equilibration/Regeneration | 500 mM NaPO4, pH 7.0 | 2.5 | 47.5 |
| 2 | Equilibration/Load/Product Recovery Flush | 10 mM NaPO4, 200 mM NaCl, pH 7.0 | 10 | 190 |
| 3 | Regeneration | 500 mM NaPO4, pH 7.0 | 5 | 95 |
| 4 | Sanitization | 0.5M NaOH | 3 | 57 |
| 5 | Storage | 0.1M NaOH | 3 | 57 |

TABLE XII

Column Restoration Protocol

| Step | Description | Mobile Phase | Column Volumes | Volume in mL |
|---|---|---|---|---|
| 1 | Pre-Equilibration/Regeneration | 500 mM NaPO4, pH 7.0 | 2.5 | 47.5 |
| 2 | Equilibration/Load/Product Recovery Flush | 10 mM NaPO4, 200 mM NaCl, pH 7.0 | 10 | 190 |
| 3 | In-Situ Restoration (ISR) | 20 mM Tris, 10 mM CaCl2, pH 8 | 2 | 38 |
| 4 | Post-ISR Wash | 10 mM NaPO4, 200 mM NaCl, pH 7.0 | 1.5 | 28.5 |
| 5 | Regeneration | 500 mM NaPO4, pH 7.0 | 5 | 95 |
| 6 | Sanitization | 0.5M NaOH | 3 | 57 |
| 7 | Storage | 0.1M NaOH | 3 | 57 |

TABLE XIII

Column Restoration Protocol

| Step | Description | Mobile Phase | Column Volumes | Volume in mL |
|---|---|---|---|---|
| 1 | Pre-Equilibration/Regeneration | 500 mM NaPO4, pH 7.0 | 2.5 | 47.5 |
| 2 | Equilibration/Load/Product Recovery Flush | 10 mM NaPO4, 200 mM NaCl, pH 7.0 | 10 | 190 |
| 3 | In-Situ Restoration (ISR) | 50 mM Tris, 10 mM CaCl2, pH 8 | 2 | 38 |
| 4 | Post-ISR Wash | 10 mM NaPO4, 200 mM NaCl, pH 7.0 | 1.5 | 28.5 |
| 5 | Regeneration | 500 mM NaPO4, pH 7.0 | 5 | 95 |
| 6 | Sanitization | 0.5M NaOH | 3 | 57 |
| 7 | Storage | 0.1M NaOH | 3 | 57 |

TABLE XIV

Column Restoration Protocol

| Step | Description | Mobile Phase | Column Volumes | Volume in mL |
|---|---|---|---|---|
| 1 | Pre-Equilibration/Regeneration | 500 mM NaPO4, pH 7.0 | 2.5 | 47.5 |
| 2 | Equilibration/Load/Product Recovery Flush | 10 mM NaPO4, 200 mM NaCl, pH 7.0 | 10 | 190 |
| 3 | In-Situ Restoration (ISR) | 100 mM Tris, 10 mM CaCl2, pH 8 | 2 | 38 |
| 4 | Post-ISR Wash | 10 mM NaPO4, 200 mM NaCl, pH 7.0 | 1.5 | 28.5 |
| 5 | Regeneration | 500 mM NaPO4, pH 7.0 | 5 | 95 |
| 6 | Sanitization | 0.5M NaOH | 3 | 57 |
| 7 | Storage | 0.1M NaOH | 3 | 57 |

TABLE XV

Results

| Resin Sample | Table Reference | Mass Change, % | Strength Change, % |
|---|---|---|---|
| Control Protocol | XI | −1.8 | −10 |
| ISR with 20 mM Tris, 10 mM CaCl2, pH 8 | XII | 2.2 | 8 |
| ISR with 50 mM Tris, 10 mM CaCl2, pH 8 | XIII | 3.8 | 20 |
| ISR with 100 mM Tris, 10 mM CaCl2, pH 8 | XIV | 4.4 | 19 |

The results in Table XV indicate that the resin treated with a control protocol experienced degradation as evidenced by a loss of mass and particle strength. Hydroxyapatite obtained from a column using the column restoration protocols in Tables XII-XIV gained in mass and particle strength compared to the control protocol (Table XI). These results demonstrate that, after a flow-through purification protocol, the use of a Tris buffered calcium solution, followed by application of a phosphate buffer and then a hydroxide provides a surprising degree of regeneration.

All patents, patent applications, and other published reference materials cited in this specification are hereby incorporated herein by reference in their entirety.

What is claimed is:

1. A method of purifying a target analyte with an apatite solid surface, wherein resin mass and particle strength are increased, the method comprising:
   (a) contacting the apatite solid surface with the target analyte, thereby separating the target analyte from one or more contaminants;
   (b) collecting the target analyte; and
   (c) after collecting the target analyte and before subsequent loading of additional target analyte, regenerating the apatite solid surface, the regenerating comprising:
      (i) contacting the apatite solid surface with a buffered calcium solution comprising a calcium ion at a concentration of at least about 1 mM and a non-zwitterionic buffer having a primary, secondary or tertiary amine, wherein the pH of the buffered calcium solution is at least about 7;
      (ii) followed by contacting the apatite solid surface with a phosphate buffered solution at a pH of at least about 6.5;
      (iii) followed by contacting the apatite solid surface with a solution comprising an alkaline hydroxide, wherein steps (c)(i), (c)(ii), and (c)(iii) increase the resin mass and particle strength of said apatite solid surface.

2. The method of claim 1, wherein (a) comprises binding the target analyte to the apatite solid surface, and (b) comprises eluting the target analyte from the apatite solid surface.

3. The method of claim 1, wherein (a) comprises binding at least 50% of the target analyte to the apatite solid surface, and (b) comprises eluting the target analyte from the apatite solid surface.

4. The method of claim 1, wherein (a) comprises contacting the apatite solid surface to the target analyte, thereby flowing the target analyte through the apatite solid surface, and (b) comprises collecting the target analyte in the flow through.

5. The method of claim 1, wherein (a) comprises contacting the apatite solid surface to the target analyte, thereby flowing at least 50% of the target analyte through the apatite solid surface, and (b) comprises collecting the target analyte in the flow through.

6. The method of claim 1, wherein the buffer in (c)(i) is a Tris containing buffer.

7. The method of claim 1, wherein the calcium ion concentration in (c)(i) is less than about 50 mM.

8. The method of claim 1, wherein the calcium ion concentration in (c)(i) is about 5 mM to about 250 mM.

9. The method of claim 1, wherein the buffered solution comprises at least one component selected from the group consisting of calcium chloride, calcium nitrate, calcium sulfate and calcium lactate.

10. The method of claim 1, wherein the buffered calcium solution is at a pH of between about 7 and about 9.

11. The method of claim 1, wherein the phosphate buffered solution comprises a solution containing from about 0.05 M to about 1.0 M phosphate at a pH of from about 6.5 to about 9.

12. The method of claim 11, wherein the phosphate buffered solution comprises 400 mM phosphate at a pH of about 7.0.

13. The method of claim 11, wherein the phosphate buffered solution comprises 500 mM phosphate at a pH of about 7.0.

14. The method of claim 1, wherein the alkaline hydroxide is at least one alkaline hydroxide selected from the group consisting of sodium hydroxide, potassium hydroxide, lithium hydroxide and ammonium hydroxide.

15. The method of claim 1, wherein the regenerating reverses, decreases or eliminates degradation of the apatite solid surface that occurs during the target analyte purification steps.

16. The method of claim 1, wherein the regenerating increases the particle strength of the apatite solid surface by at least about 1% as determined by uniaxial confined bulk compression (UCBC).

17. The method of claim 1, wherein step(c) is performed before, or replaces, a phosphate cleaning/stripping step that elutes adsorbed biological compounds.

18. The method of claim 1, wherein contacting the apatite solid surface with a solution comprising phosphate at a pH of at least about 6.5 further comprises:
   contacting the apatite solid surface with a solution comprising phosphate at a concentration of about 10 mM, at a pH of at least about 6.5; and
   then contacting the apatite solid surface with a solution comprising phosphate at a concentration of at least about 100 mM at a pH of at least about 6.5.

19. The method of claim 1, further comprising washing the apatite solid surface with a wash solution prior to the regenerating step, the wash solution comprising phosphate at a concentration of less than about 100 mM, at a pH of at least about 6.5.

20. The method of claim 1, wherein the regenerating consists of step(c)(i), followed by contacting the apatite solid surface with a wash solution, then step(c)(ii), and then step(c)(iii).

\* \* \* \* \*